US009486597B2

(12) United States Patent
Lieberman et al.

(10) Patent No.: US 9,486,597 B2
(45) Date of Patent: Nov. 8, 2016

(54) AEROSOL DELIVERY MASK

(75) Inventors: Eric A. Lieberman, Scotch Plains, NJ (US); Dirk von Hollen, Clark, NJ (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 1395 days.

(21) Appl. No.: 12/019,939

(22) Filed: Jan. 25, 2008

(65) Prior Publication Data
US 2008/0178886 A1  Jul. 31, 2008

Related U.S. Application Data

(60) Provisional application No. 60/898,306, filed on Jan. 30, 2007.

(51) Int. Cl.
| *A61M 16/06* | (2006.01) |
| *A61M 16/08* | (2006.01) |
| *A61M 11/00* | (2006.01) |
| *A61M 15/00* | (2006.01) |

(52) U.S. Cl.
CPC ......... *A61M 16/06* (2013.01); *A61M 16/0616* (2014.02); *A61M 16/0833* (2014.02); *A61M 11/00* (2013.01); *A61M 15/00* (2013.01); *A61M 16/0683* (2013.01)

(58) Field of Classification Search
CPC .. A61M 16/0605–16/0622; A61M 2016/0661
USPC ............ 128/200.24, 201.23, 203.29, 205.25, 128/206.21, 206.24, 206.26, 206.28
See application file for complete search history.

(56) References Cited

U.S. PATENT DOCUMENTS

| 2,749,910 | A | * | 6/1956 | Faulconer, Jr. ................. 601/44 |
| 3,556,097 | A | * | 1/1971 | Wallace .................... 128/202.23 |
| 3,695,264 | A | * | 10/1972 | Laeral ..................... 128/202.28 |
| 4,470,413 | A | * | 9/1984 | Warncke .................. 128/201.18 |
| 4,907,584 | A | * | 3/1990 | McGinnis ................ 128/206.24 |
| 5,921,239 | A | * | 7/1999 | McCall et al. ........... 128/205.25 |
| 6,581,594 | B1 | | 6/2003 | Drew et al. |
| 6,631,713 | B1 | * | 10/2003 | Christopher ............ 128/200.21 |
| 6,860,268 | B2 | * | 3/2005 | Bohn et al. .............. 128/206.21 |
| 2005/0172969 | A1 | * | 8/2005 | Ging et al. .............. 128/206.24 |
| 2005/0199239 | A1 | | 9/2005 | Lang et al. |
| 2005/0199240 | A1 | * | 9/2005 | Hall ........................ 128/206.26 |
| 2005/0263150 | A1 | | 12/2005 | Chathampally et al. |
| 2007/0163594 | A1 | * | 7/2007 | Ho et al. .................. 128/206.24 |
| 2007/0221226 | A1 | * | 9/2007 | Hansen et al. ........... 128/206.21 |
| 2009/0032024 | A1 | * | 2/2009 | Burz et al. ............... 128/206.24 |

FOREIGN PATENT DOCUMENTS

| JP | 58174142 U | 11/1983 |
| WO | 2006074513 A1 | 7/2006 |

* cited by examiner

*Primary Examiner* — Valerie L Woodward
(74) *Attorney, Agent, or Firm* — Michael W. Haas

(57) ABSTRACT

The present invention provides a mask for sealing an area around a patient's mouth and nose for delivery of an aerosol. The mask includes a mask body having an opening for reception of the aerosol and a mask seal configured to engage a patient's face around the nose and mouth. An adapter is arranged to be removably attached to the mask body for removably coupling the mask body to an aerosol delivery device.

25 Claims, 21 Drawing Sheets

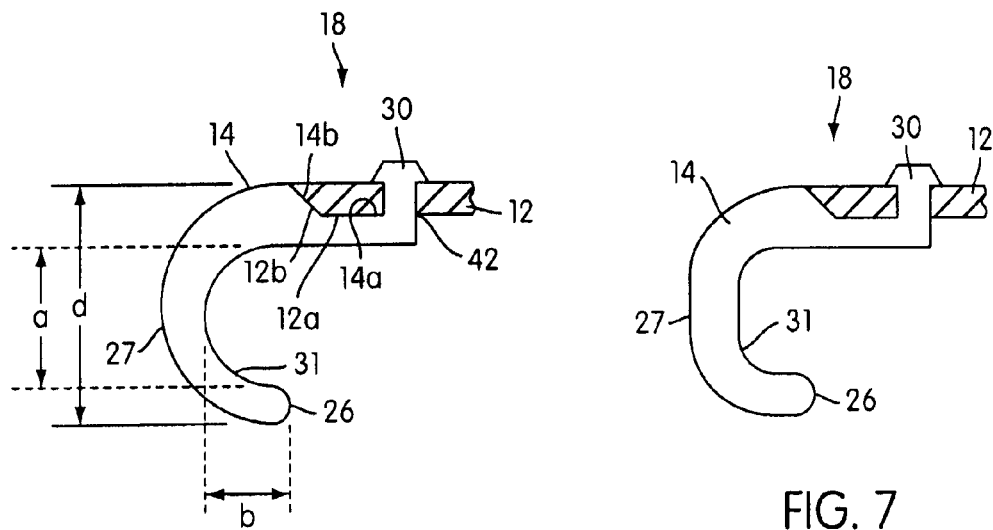
FIG. 6
FIG. 7
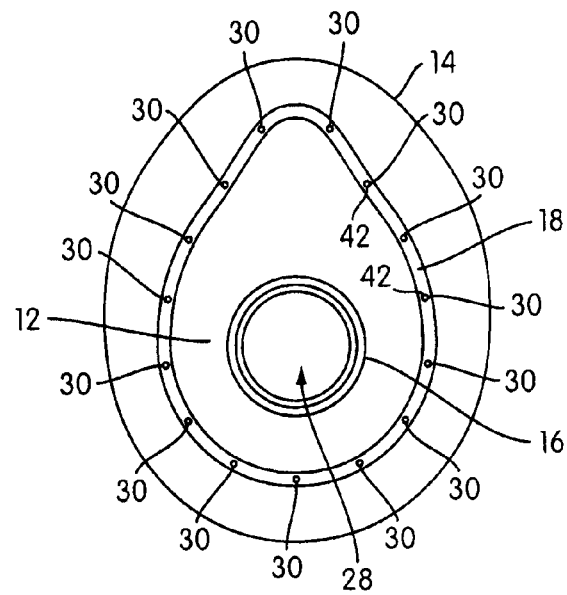
FIG. 8

SECTION A-A  SECTION B-B  SECTION C-C

SECTION D-D   SECTION E-E   SECTION F-F

SECTION K-K

SECTION I-I

SECTION J-J

SECTION H-H

SECTION G-G

SECTION P-P

SECTION N-N

SECTION O-O

SECTION M-M

SECTION L-L

AEROSOL DELIVERY MASK

CROSS-REFERENCE TO RELATED APPLICATIONS

This application claims priority under 35 U.S.C. § 119(e) from provisional U.S. patent application No. 60/898,306 filed Jan. 30, 2007 the contents of which are incorporated herein by reference.

BACKGROUND OF THE INVENTION

1. Field of the Invention

The present invention relates to aerosol delivery systems and, more particularly, to a mask that forms a seal with a patient's face during aerosol delivery.

2. Description of the Related Art

Conventional nebulizers, spacers, and other aerosol delivery mechanisms with masks allow aerosolized medication to be blown into a patient's eyes. Accordingly, there exists a need in the art for a mask that communicates with the patient and with the aerosol delivery mechanism to prevent aerosolized medication from being blown into a patient's eyes.

SUMMARY OF THE INVENTION

It is an object of the present invention to provide a mask that overcomes the shortcomings of conventional devices. This object is achieved according to one embodiment of the present invention by providing a mask for sealing an area around a patient's mouth and nose for delivery of an aerosol that includes a mask body that has an opening for reception of the aerosol and a mask seal that is configured to engage a patient's face around the nose and mouth. The seal has a configuration that includes a generally larger radiused lower portion for engagement of the patient's face between the chin and lips and upwardly along opposite sides of the patient's mouth, a generally smaller radiused upper portion for engagement of the patient's face across the bridge of the patient's nose, and a transition portion between the lower portion and the upper portion for engagement of the patient's nose and beneath the eyes. The transition portion of the mask seal portion has more material in its cross section than the lower portion.

It is another object of the present invention to provide a mask for sealing an area around a patient's mouth and nose for delivery of an aerosol that includes a mask body having an opening for reception of the aerosol and a mask seal configured to engage a patient's face around the nose and mouth. The seal has a configuration that includes a generally larger radiused lower portion for engagement of the patient's face between the chin and lips and upwardly along opposite sides of the patient's mouth, a generally smaller radiused upper portion for engagement of the patient's face across the bridge of the patient's nose, and a transition portion between the lower portion and the upper portion for engagement of the patient's nose and beneath the eyes. The lower portion has a distal face engaging surface that extends generally along a plane, and the transition portion has a distal face engaging surface that bulges outwardly from the plane.

It is yet another object of the present invention to provide a mask for sealing an area around a patient's mouth and nose for delivery of an aerosol that includes a mask body having an opening for reception of the aerosol and a mask seal configured to engage a patient's face around the nose and mouth. The seal has a configuration that includes a generally larger radiused lower portion for engagement of the patient's face between the chin and lips and upwardly along opposite sides of the patient's mouth, a generally smaller radiused upper portion for engagement of the patient's face across the bridge of the patient's nose, and a transition portion between the lower portion and the upper portion for engagement of the patient's nose and beneath the eyes. The transition portion of the mask seal portion undergoes a greater displacement in comparison with the lower portion of the mask seal portion when the seal portion is disposed in sealing engagement with the patient's face.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 6 is a cross-sectional view of a connection between the mask body and mask seal portion in accordance with an embodiment of the present invention;

FIG. 7 is a cross-sectional view of a connection between the mask body and mask seal portion in accordance with another embodiment of the present invention;

FIG. 8 is a front elevational view of a mask with a barbed attachment region in accordance with an embodiment of the present invention;

DETAILED DESCRIPTION OF THE EXEMPLARY EMBODIMENTS

Figure 1:
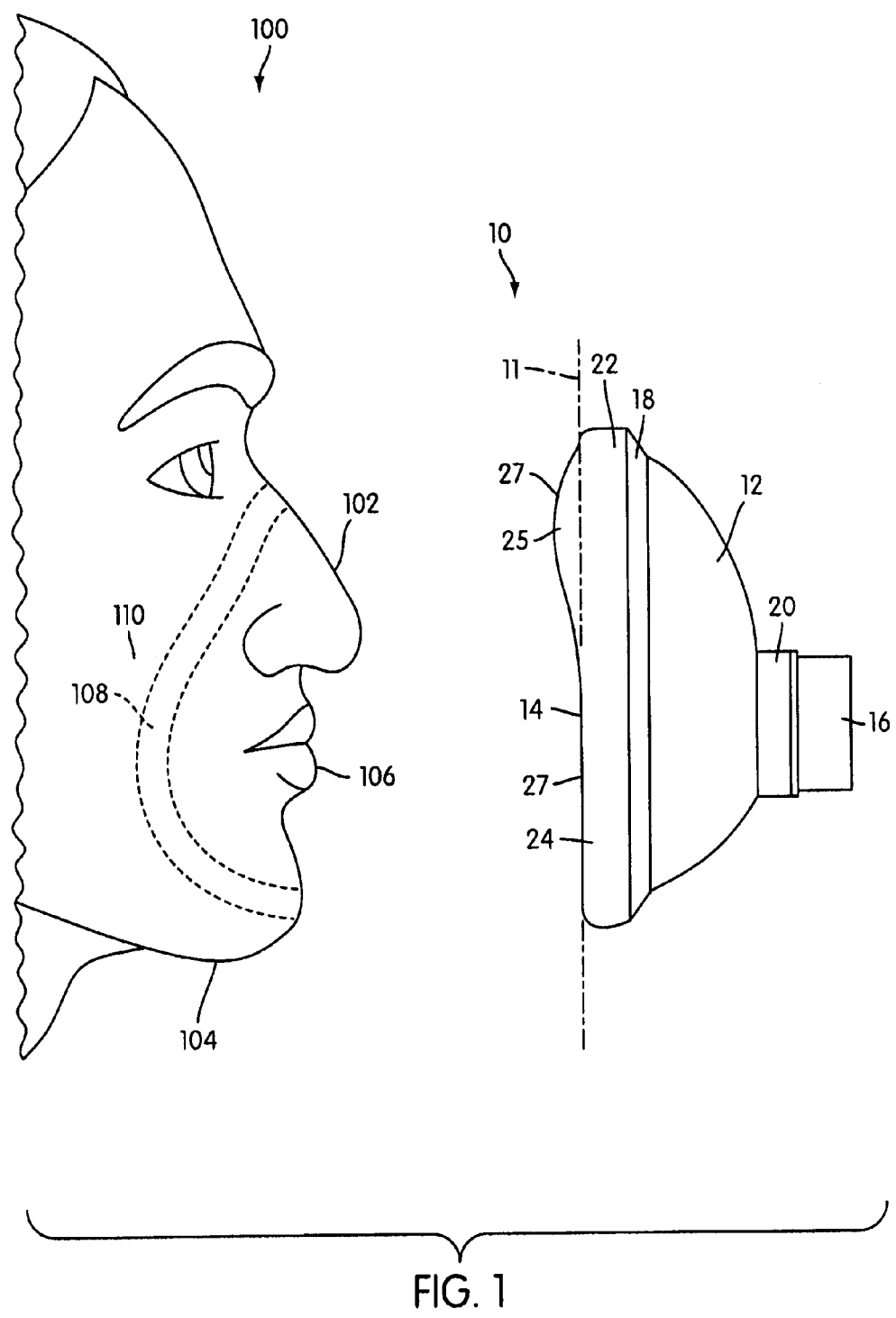
FIG. 1 is a side elevational view of a mask and patient's face in accordance with an embodiment of the present invention.
Figure 2:
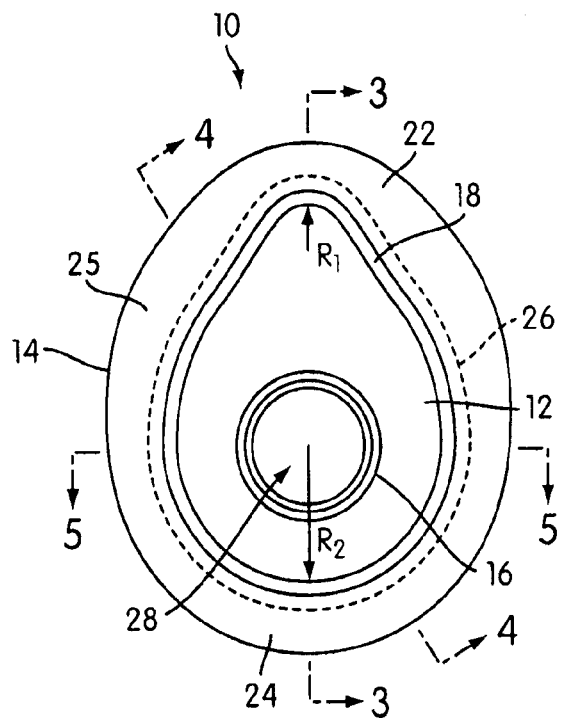
FIG. 2 is a front elevational view of a mask in accordance with an embodiment of the present invention.

FIGS. 1-2 show a mask 10 for use in aerosol delivery in accordance with an embodiment of the present invention. The mask 10 may generally include a mask body 12, a seal portion 14, and an adapter 16. The mask 10 is configured to be placed against a patient's face 100 in an engagement region 108 that extends from between the chin 104 and lips 106, upwardly along region 110 on opposite sides of the patient's mouth, and across the nose 102 and over the bridge of the nose, as shown. The seal portion 14 may be attached to the mask body 12 at an attachment region 18, as shown in FIG. 2. The attachment region 18 may be along the perimeter or edge of the mask body 12 and along a perimeter or edge of the seal portion 14, such that there is some overlap of the respective edges of the mask body 12 and the seal portion 14, as shown. Accordingly, there is some material of the mask body 12 that engages with some material of the seal portion 14, such that a layered connection is formed. Other embodiments are contemplated in which there is no overlap, such as by attaching the mask body 12 and seal portion 14 with their edges end to end (e.g., by an adhesive connection). On a side of the mask body 12 that is opposite from the seal portion 14, the mask body 12 has an opening 28 (see FIG. 2) for receipt of an adapter 16. The adapter 16 can be of various sizes, shapes, and configurations, and thus may be used to connect or otherwise communicate the mask 10 to different aerosol delivery systems or devices, such as nebulizers, spacers, aerosol dispensers, or other suitable devices.

The seal portion 14 and mask body 12 may be sized to enclose a patient's mouth and nose. One of ordinary skill in the art will appreciate that the configuration of the mask may vary and is not limited to a particular size or configuration, as patients may range in age, size, and/or medical purpose so as to require appropriate selection from among a variety of different mask sizes and configurations.

The seal portion 14 may be made of a relatively soft and/or flexible material so that the seal portion 14 conforms to the shape of a patient's face when held against it. The seal portion 14 may be made of, for example, silicone or an elastomeric material. As shown in the cross-sectional views of FIGS. 6 and 7, the seal portion 14 may have an arcuate or partially tubular cross-sectional configuration (also referred to as a concavo-convex cross-section, having a generally concave inner surface and generally convex outer surface). In the embodiment of FIG. 6, the seal portion 14 has a generally rounded, convex face engaging surface 27 for advantageous sealing characteristics. In the embodiment of FIG. 7, the face engaging surface 27 has a more flattened, convex configuration. Also, different regions of the seal portion 14 around the perimeter of the mask body 12 may have different cross-sectional configurations. Various other seal portion configurations will become apparent to those skilled in the art.

The mask body 12, in one embodiment, is made of a relatively more rigid material (higher durometer material) than the seal portion 14. For example, mask body 12 may be made from polycarbonate, or other suitable material. The mask body 12 provides structural rigidity to the mask 10 and, in some embodiments, may be a portion of a disposable mask that is retained when replacing the seal portion 14.

The mask 10 may be formed by a two-step insert molding process. For example, the relatively harder mask body 12 may be molded first and then inserted into a second mold for the seal portion 14, which is injection molded to form around and/or into the mask body 12.

In one embodiment, the seal portion 14 is generally oblong or pear shaped, as shown in FIG. 2. The seal portion 14 accordingly includes an upper portion 22, a lower portion 24, and a transition portion 25. The upper portion 22, which may be configured to engage a patent's face across the bridge of the patient's nose, has a radius of curvature R1 that is relatively smaller than the radius of curvature R2 of the lower portion 24. The lower portion 24, which may be configured to engage a patent's face between the chin and the lips and upwardly along opposite sides of the mouth and along the cheeks, has a radius of curvature that is relatively larger the than the upper portion 22. The transition portion 25 extends generally from the upper portion 22 to the lower portion 24 and engages the patient's nose and beneath the eyes. This transition portion 25 of the seal portion 14 has more material in its cross-section, and has a greater linear length (i.e., if the seal portion were to be unrolled or straightened into a linear configuration) when measured in a direction extending orthogonally away from the mask body, than each of the upper portion 22 and the lower portion 24, so as to effectively block medication from reaching a patient's eyes.

An end 26 of the seal portion 14 is shown in FIG. 6 as having an outer surface being a distance d from the outer surface of the seal portion at the interface 18 with the mask body 12 (end 26 is also shown in FIG. 2 by dashed lines). As shown in FIG. 1, the transition portion 25 of the mask 10 is configured to engage a patient's nose 102 and comprises a section of seal portion 14 that defines a well (i.e., the concave interior) that is wider and deeper than the upper and lower regions of the seal portion 14. Accordingly, the distance d may be larger in the transition portion 25 than it is in other parts of the seal portion 14, such as upper portion 22 and/or the lower portion 24. In this manner, the mask 10 effectively seals the nose and mouth area by providing extra material in the seal portion 14 to compensate for the contours of a patient's face.

Figure 3:
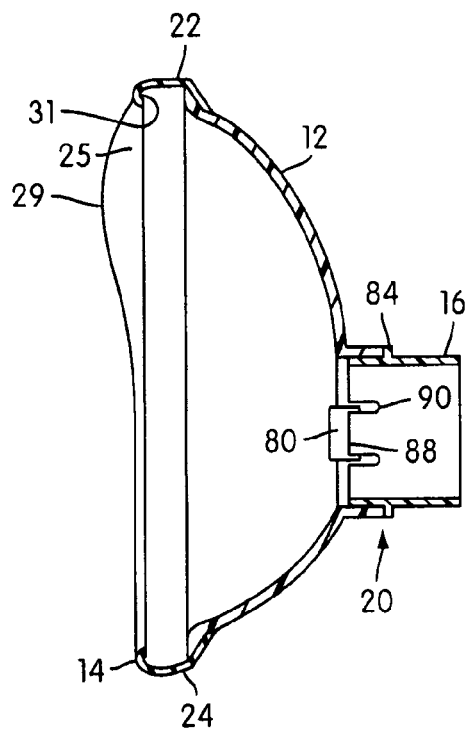
FIG. 3 is a cross-sectional view along line 3 in FIG. 2 of a mask in accordance with an embodiment of the present invention.
Figure 4:
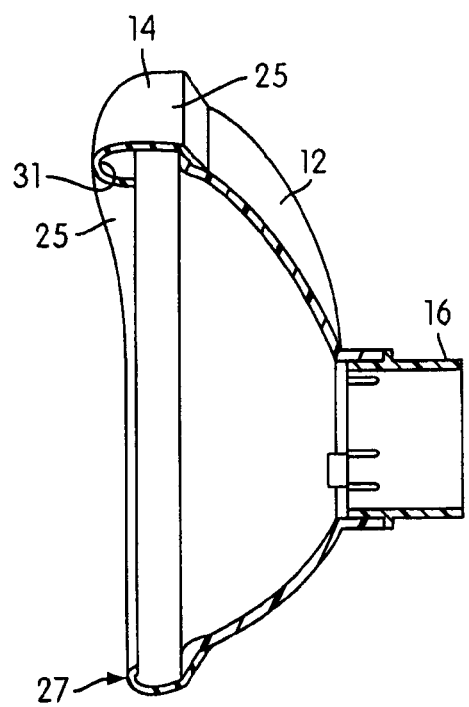
FIG. 4 is a cross-sectional view along line 4 in FIG. 2 of a mask in accordance with an embodiment of the present invention.
Figure 5:
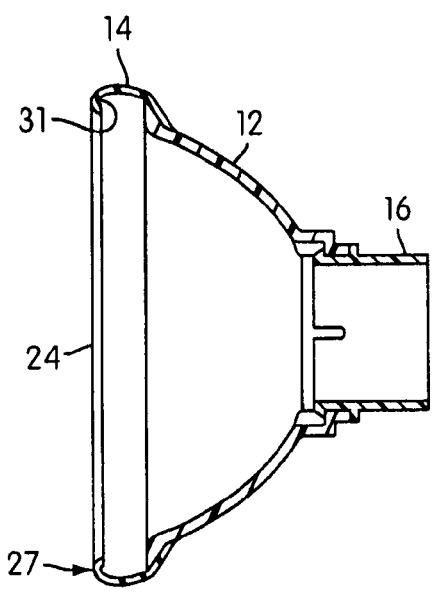
FIG. 5 is a cross-sectional view along line 5 in FIG. 2 of a mask in accordance with an embodiment of the present invention.

FIGS. 3-5 are cross-sectional views of mask 10 taken along various lines in FIG. 2 illustrating the structure of the transition portion 25 of the mask 10. As shown in FIG. 3, an inner concave surface 31 of the seal portion forms a relatively shallow well in an upper portion 22 and a lower portion 24 (i.e., the dimension b, as indicated in FIG. 6, is relatively small in those regions). Additionally, the width of the curved seal portion 14 in those portions is relatively small as well (i.e., the dimensions a and d as indicated in FIG. 6). FIG. 4, on the other hand, which represents a cross-sectional view through the transition portion 25 of the mask 10 (towards the upper portion of the Figure), illustrates that the seal portion 14 in the transition portion 25 is both wider and has a deeper well. In FIG. 5, it is shown that the seal portion 14 has a relatively shallow well and is less wide at the lower portion 24 as compared to the transition portion 25.

FIGS. 27 and 28 show cross-sectional measurements of one embodiment of a mask manufactured in accordance with the teachings herein. FIG. 27 illustrates a series of parallel cross-sectional views taken longitudinally and parallel with respect to the longer (longest) dimension of the mask (from top region to bottom region). FIG. 27 shows various dimensions, measured in inches. The dimensions shown include the depth of the seal well (e.g., dimension b in FIG. 6), the total depth of the mask 10, the outer diameter or dimension of the mask 10, and the distance from the distal end of the face engaging surface 27 of the seal portion 14 and the connection region 18 with the body 12. For example, FIG. 27 illustrates that the depth of the well at one longitudinal section of the transition region is 0.271 inches (through Section D-D), while the depth of the well through one section of the lower region is 0.113 inches (through Section B-B). In addition, in Section D-D, for example, the distance between the distal end of the face engaging region 27 and the connection of the seal portion with the mask body is about 0.749 inches at the transition region, while it is about 0.557 inches at the lower region.

FIG. 28 illustrates a series of parallel cross-sections taken laterally and perpendicular to the longer (longest) dimension of the mask. It should be appreciated that for the particular embodiment shown, the dimensions illustrated in FIGS. 27 and 28 may be varied by ±10%. FIG. 28 shows various dimensions, including the outer diameter of the seal portion 14, the inner diameter of the seal portion 14, the width of the seal well (e.g., dimension a in FIG. 6), and the total depth of the mask 10 at various cross-sections through the mask.

FIGS. 27 and 28 are drawn in proper proportion in accordance with one embodiment, although drawn at a scale that is less than 1:1. Thus, FIGS. 27 and 28 as set forth herein disclose fully claimable subject matter, not only in terms of the numeric dimensions illustrated within a range of ±10%, but also for the relative proportions shown, and the corresponding extrapolated numeric dimensions that may be derived by physical measurement of the FIGS. 27 and 28.

The transition portion 25 is shown with respect to a notional plane 11 in FIG. 1. As shown, with additional reference to FIG. 6, the lower portion 24 has an outermost surface or distal face engaging surface 27 that extends generally along the plane 11. The transition portion 25, in contrast, has the distal face engaging surface 27 that bulges outwardly from the plane 11 to conform to the contours of a patient's face. Due to the dimensions and configurations of the seal, the bulging transition portion 25 is pre-loaded or pre-stressed against the patient's face when pressure is developed within the mask. In other words, the larger surface areas of the enlarged transition portion 25 will have a greater force applied thereto, and the seal will "bottom out" or seal against the patient's face more quickly in that region in comparison with other regions of the seal 14. Also, because the transition region 25 bulges towards the patient's face, a greater sealing force will exist at the transition portion 25 in comparison with other regions. By enhancing the sealing characteristics of the transition portion 25 in comparison with other regions of the seal 14, there is less likelihood that aerosolized medication will be blown into the eyes of the patient.

Because more material is provided at the transition portion 25 of the seal portion 14, the seal transition portion 25 is capable of greater deformation and displacement in relation to the seal lower portion 24 and upper portion 22. As a result, the face engaging surface 27 at the transition portion 25 is able to generate a greater surface area of contact with the face to reduce the likelihood/amount of gas escaping therebeyond. As a result, gaseous medication is substantially prevented from blowing into the patient's eyes.

In addition, in one embodiment, at the transition portion 25 the inner concave surface 31 of the seal portion 14 presents a greater internal effective surface area (see dimension "a" in FIG. 6) than the concave surface 31 presents at the lower portion 24 and upper portion 22. As a result, the pressure formed between the mask 10 and the patient's face may apply a greater force against the patient's face at the transition portion 25 in comparison with the lower portion 24 and upper portion 22.

As noted previously, FIGS. 27 and 28 show series of vertical and horizontal cross-sectional views, respectively, taken along progressive planes of a mask in accordance with an embodiment of the present invention. Dimensions shown are understood to be merely exemplary and are not intended to limit the invention. One of skill in the art will appreciate that mask dimensions may vary greatly from those indicated and be within the scope of the present invention. FIG. 27 is particularly useful in illustrating the widening and deepening of the transition portion 25 (see FIG. 2) as one moves away from the upper portion 22 towards the transition portion 25, and the return to a more shallow and thinner region as one moves away from the transition portion 25 and toward the lower portion 24. FIG. 28 is similarly useful in showing that the seal portion 14 is generally uniform in terms of having a relatively small width and shallow depth in the face engaging region of the lower portion 24 and that the face engaging region is deeper and wider in the transition portion 25.

As is shown in FIGS. 6-9, the seal portion 14 may be fastened to the mask body 12 by a series of barbs 30 integrally formed with the seal portion 14 and extending through holes 42 in the attachment region 18 of the mask body 12. The seal portion 14 and the mask body 12 may be configured with complementary shaped structure and may, in some embodiments, be secured to each other adhesively, such as with a glue or epoxy, or by heat or chemical treatment. An internal surface 12a of the mask body 12 may abut an external surface 14a of the seal portion. Angled mask body surface 12b may also be configured to engage with a complementary seal portion angled surface 14b. In one embodiment, the internal surfaces 12a and 14a and/or the angled surfaces 12b and 14b may be adhesively fastened to each other to provide a permanent connection. In another embodiment, no adhesive is used, and the barbs 30 in holes 42 provide a mechanical lock sufficient to secure the mask body 12 to the seal 14.

Figure 9:
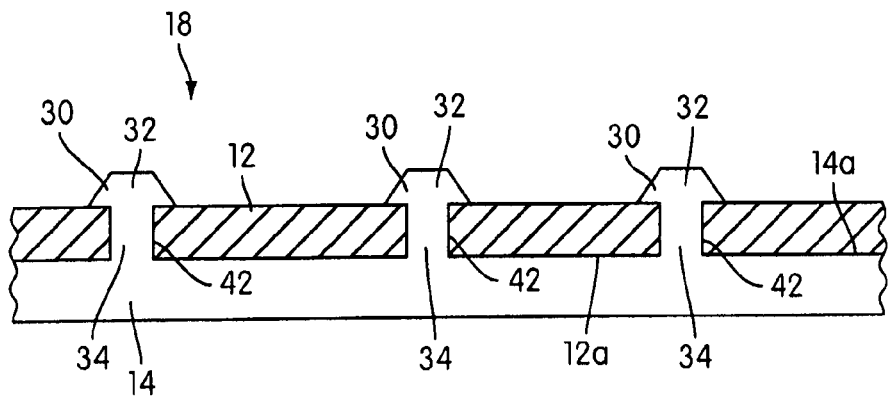
FIG. 9 is a cross-sectional view of an attachment region of a mask in accordance with an embodiment of the present invention.

An exemplary system of barbs 30 and holes 42 suitable for attachment of the seal portion 14 to the mask body 12 is shown in top view in FIG. 8 and in cross sectional view in FIG. 9. As shown, a plurality of barbs 30 are disposed around the attachment region 18 between the seal portion 14 and the mask body 12. FIG. 9 shows a continuous edge of the seal portion 14 having barbs 30 disposed thereon and fastened to the mask body 12 through holes 42.

Figure 10:
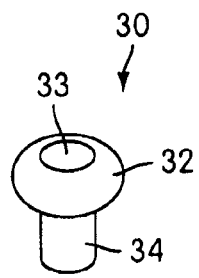
FIG. 10 is a perspective view of a barb in accordance with an embodiment of the present invention.

With additional reference to FIG. 10, the barbs 30 are shown as comprising a head 32 and stem 34. The head 32 has a greater diameter, at least at the lower portion thereof, than the diameter of the corresponding hole 42 into which it is inserted. The stem 34 has a diameter that is of approximately the same dimension as the diameter of hole 42, although it may be slightly larger or smaller. During attachment, the head 32 is compressed upon insertion into the hole 42. When the head 32 clears the hole 42, it returns to its expanded condition and thereby prevents detachment of the seal portion 14 from the mask body 12 under normal circumstances. As seen in FIG. 10, the barbs 30 may optionally be further provided with a bore 33 through their center in order to accommodate displacement of the outwardly extending head 32 during compression and passage through the hole 42.

Figure 11:
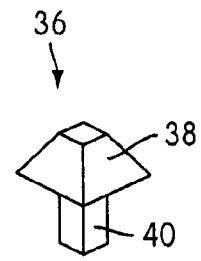
FIG. 11 is a perspective view of a barb in accordance with another embodiment of the present invention.

FIG. 11 shows a barb 36 in accordance with another embodiment of the present invention, which has a squared head 38 and stem 40. The squared barb 36 and the rounded barb 30 are merely exemplary of the various shapes and configurations for barbs that may be used to attach the seal portion 14 to mask body 12. The configurations disclosed herein should not be considered limiting as one skilled in the art will appreciate that any suitably shaped barb may perform the functions as disclosed herein, and other structures for connection can be used.

Various other exemplary constructions and methods for securing the seal portion 14 to the mask body 12 are further illustrated, for example, in FIGS. 12-19. Various alterations and substitutions will become apparent to those skilled in the art and are within the scope of the present invention.

Figure 12:
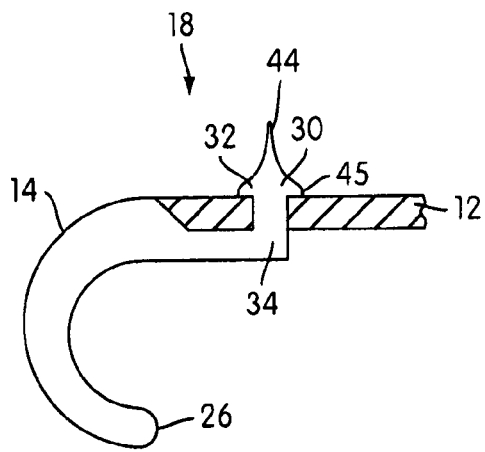
FIG. 12 is a cross-sectional view of a connection between the mask body and mask seal portion in accordance with a further embodiment of the present invention.

The attachment region 18 shown in FIG. 12 is similar to that of FIG. 6, and further includes a narrowly tapered upper end portion 44 attached to or formed integrally with the lower portion 45 of the head 32. The tapered portion 44 has a diameter that is smaller than the diameter of hole 42, while the lower portion 45 of the head has a greater dimension than the hole 42. The tapered portion 44 also has a length that is longer than the axial length of hole 42. The tapered portion 44 facilitates attachment of the seal portion 14 by allowing a user to grip the tapered portion 44 through the hole 42 and pull the wider part of the head 32 through the hole 42.

Figure 13:
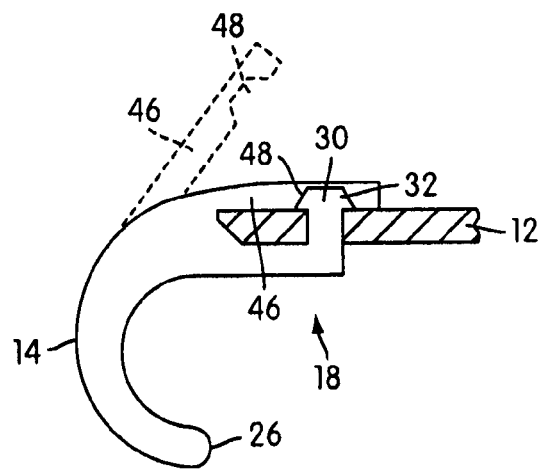
FIG. 13 is a cross-sectional view of a connection between the mask body and mask seal portion in accordance with a further embodiment of the present invention.

FIG. 13 shows a seal portion 14 and mask body 12 attachment region 18 similar to that shown in FIG. 6, and further includes a flap 46 that covers the head 32 of the barb 30. The flap 46 may have a cutout 48 that corresponds to shape and size of the barb 30 such that, when placed over the barb 30, the barb 30 nests into the cutout 48. The flap 46 may be connected to mask body 12 adhesively to further establish a secure attachment.

Figure 14:
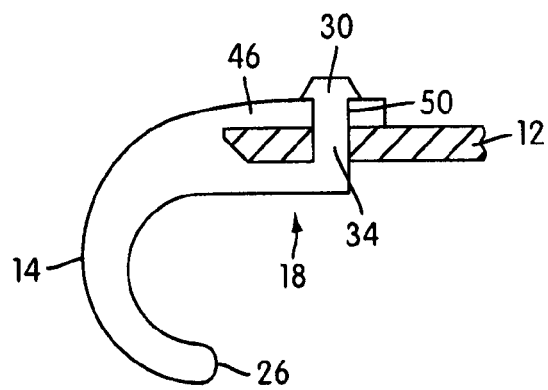
FIG. 14 is a cross-sectional view of a connection between the mask body and mask seal portion in accordance with a further embodiment of the present invention.

FIG. 14 shows a seal portion 14 and mask body 12, with attachment region 18 similar to that shown in FIG. 13. The attachment region 18 further includes a hole 50 through the flap 46 and a longer barb stem 34 in comparison to the embodiment of FIG. 13. As such, the barb 30 is configured to pass through both the mask body 12 (through hole 42, as above) as well as the flap 46 (through hole 50).

Figure 15:
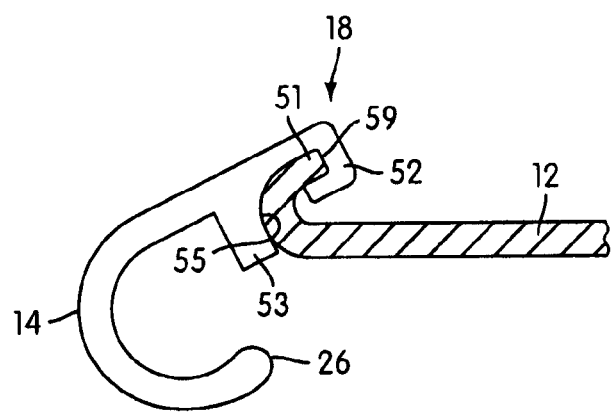
FIG. 15 is a cross-sectional view of a connection between the mask body portion and the mask seal portion pierced flap in accordance with a further embodiment of the present invention.

FIG. 15 shows a seal portion 14 and mask body 12 attachment region 18 according to an alternative embodiment of the present invention. In this embodiment, the edge of the mask body 12 curves upwardly to form an arcuate lip 51. The seal portion 14 has a correspondingly shaped recess 55 defined in part by a hook portion 52 that wraps around the end edge 59 of lip 51, and abutment portion 53 in order to secure itself on the lip 51. The seal portion 14 and the mask body 12 may be adhesively joined in order to further secure the attachment.

Figure 16:
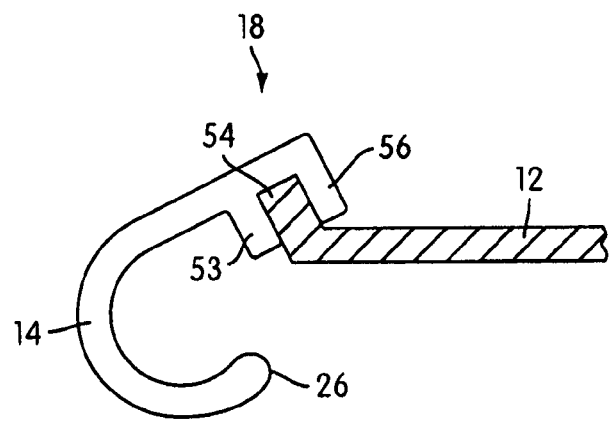
FIG. 16 is a cross-sectional view of a connection between the mask body portion and the mask seal portion in accordance with a further embodiment of the present invention.

FIG. 16 shows a seal portion 14 and mask body 12 attachment region 18 similar to that shown in FIG. 15 and includes an edge of the mask body 12 that is angled outwardly to form a bent lip 54. The seal portion 14 similarly includes an abutment 53 and corresponding structure in the form of a second abutment 56 instead of a hook 52 as shown in FIG. 15. The seal portion 14 and the mask body 12 may likewise be adhesively joined in order to further secure the attachment.

Figure 17:
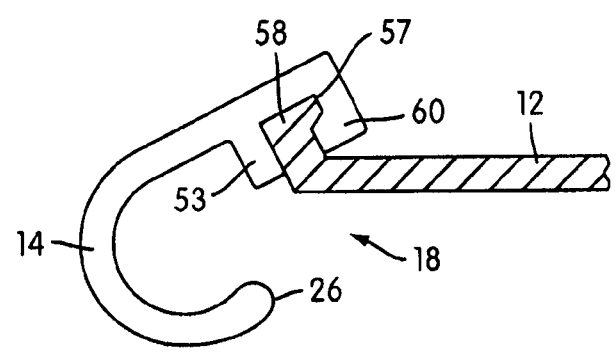
FIG. 17 is a cross-sectional view of a connection between the mask body portion and the mask seal portion in accordance with a further embodiment of the present invention.

FIG. 17 shows a seal portion 14 and mask body 12 attachment region 18 similar to that shown in FIG. 16. Specifically, rather than the bent lip 54 of FIG. 16, the embodiment has a bent lip with an additional protruding ridge 57 to form a ridged lip 58, thereby increasing the surface area of the mating surfaces while providing more of an interlocking fit with hook portion 60. The seal portion 14 and the mask body 12 may likewise be adhesively joined in order to further secure the attachment.

Figure 18:
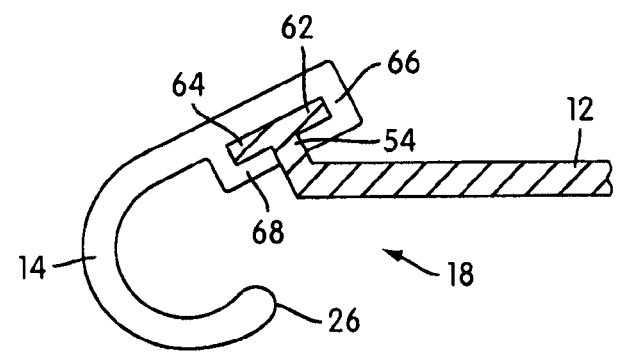
FIG. 18 is a cross-sectional view of a connection between the mask body portion and the mask seal portion in accordance with a further embodiment of the present invention.

FIG. 18 shows a seal portion 14 and mask body 12 attachment region 18 that includes an angled edge 54 that includes an upper flange 62 and a lower flange 64 to form a T-shaped lip. The seal portion 14 may include an upper hook portion 66 and a lower hook portion 68 to define a cavity that encloses the respective flanges or T-shaped lip on the mask body 12. The seal portion 14 and the mask body 12 may likewise be adhesively joined in order to further secure the attachment.

Figure 19:
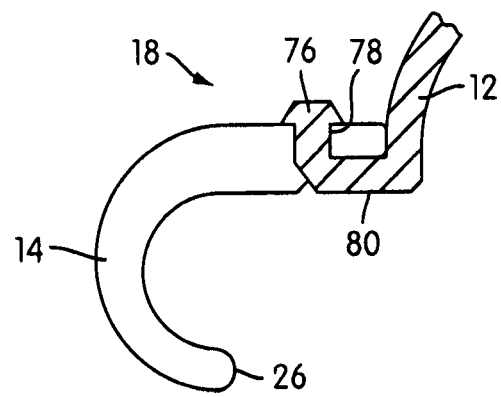
FIG. 19 is a cross-sectional view of a connection between the mask body portion and the mask seal portion in accordance with a further embodiment of the present invention.

FIG. 19 shows a seal portion 14 and mask body 12 attachment region in accordance with another embodiment of the present invention. In this embodiment, it is the mask body 12 that carries a barb 76, which passes through a hole or piercing 78 in the seal portion 14. As shown, the mask body 12 includes an outwardly extending lip portion 80, which has thereon an upwardly extending barb 76. Although shown as including a lip portion 80 extending from the mask body 12, it is appreciated that barbs 76 may extend directly from the main body of the mask body 12 or that barbs 76 may be attached to a further or multiple further lips or legs as one of skill in the art may recognize as providing satisfactory strength or fastening characteristics. The seal portion 14 and the mask body 12 may be adhesively joined in order to further secure the attachment.

Figure 20:
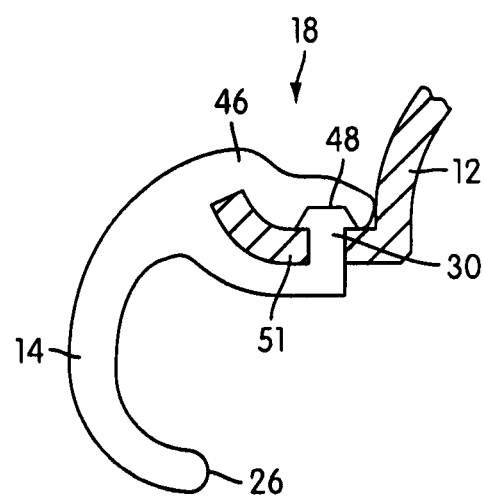
FIG. 20 is a cross-sectional view of a connection between the mask body portion and the mask seal portion in accordance with a further embodiment of the present invention.

FIG. 20 shows a seal portion 14 and mask body 12 attachment region 18 with flap 46 similar to that shown in FIG. 13, and further combines the arcuately curved lip 51 similar to that shown in FIG. 15. The flap 46 may be configured to extend over the lip 51 and include a cutout 48 to be contoured with the barb 30 such that the barb 30 nests in the cutout 48. In one embodiment, the barb 30 may additionally pass through the flap 46 in a manner similar to the embodiment shown in FIG. 14. The seal portion 14 and the mask body 12 may be adhesively joined in order to further secure the attachment.

Figure 21:
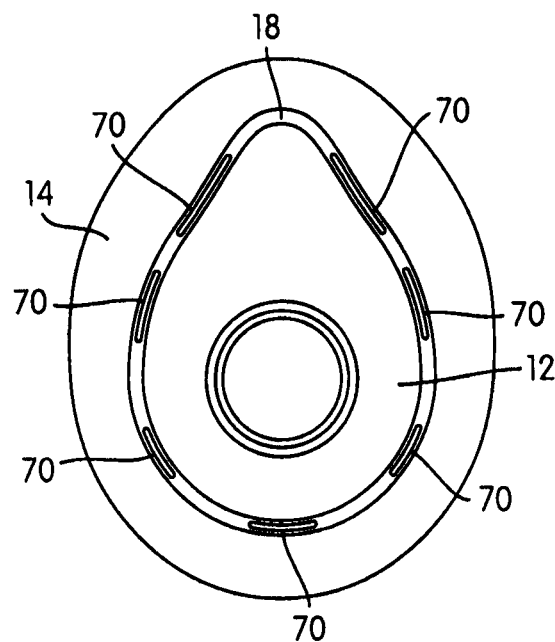
FIG. 21 is a front elevational view of a mask having elongated barbs in an attachment region in accordance with an embodiment of the present invention.
Figure 22:
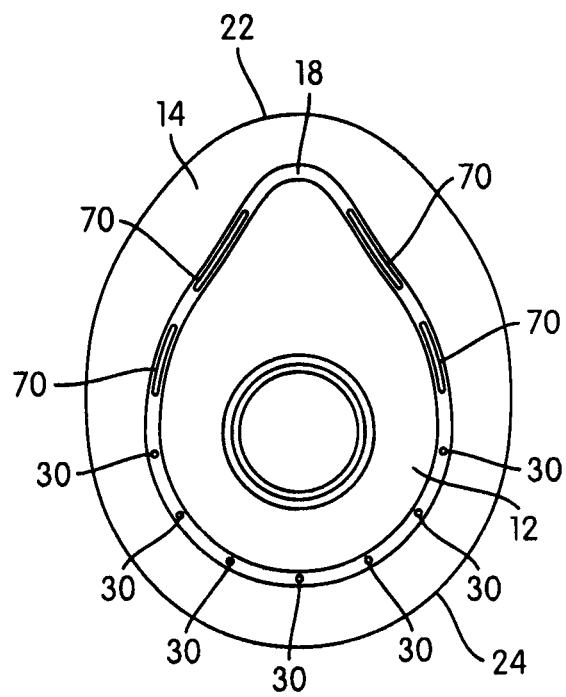
FIG. 22 is a front elevational view of a mask having elongated barbs and single point barbs in accordance with an embodiment of the present invention.
Figure 23:
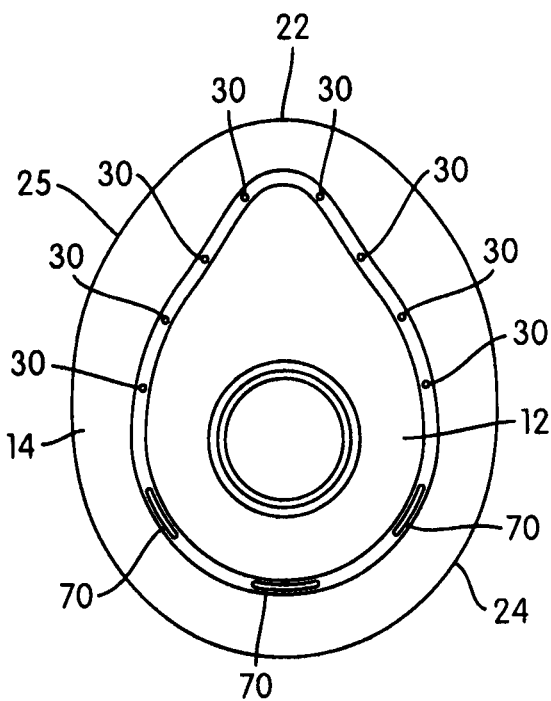
FIG. 23 is a front elevational view of a mask having elongated barbs and single point barbs in accordance with another embodiment of the present invention.

As shown in FIGS. 21-24, alternative configurations may be utilized with respect to the placement and particulars of the barbs. FIG. 21 shows a plurality of elongated barbs 70 disposed along the attachment region 18 of the mask 10 instead of the shorter, point barbs 30 as shown in FIG. 8. FIG. 22 shows a combination of elongated barbs 70 and shorter point barbs 30, with the elongated barbs 70 being disposed generally in the upper portion 22 and the transition portion 25 of the mask 10 and the shorter point barbs disposed generally in the lower portion 24 of the mask 10. FIG. 23 shows a combination of elongated barbs 70 and shorter point barbs 30 with the elongated barbs 70 being disposed generally in the lower portion 24 of the mask 10 and the shorter point barbs disposed generally in the upper portion 22 and the transition portion 25 of the mask 10.

Figure 24:
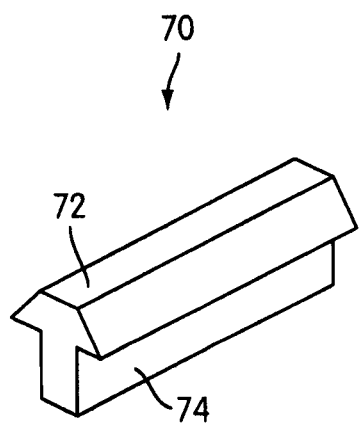
FIG. 24 is a perspective view of an elongated barb in accordance with an embodiment of the present invention.

FIG. 24 is a perspective view of an elongated barb 70 in accordance with the preceding embodiments. As shown, the barb 70 includes a head portion 72 and a stem portion 74. The elongated barbs 70 may be applied to any of the attachment mechanisms described above and are equally applicable to all embodiments disclosed herein.

Figure 25:
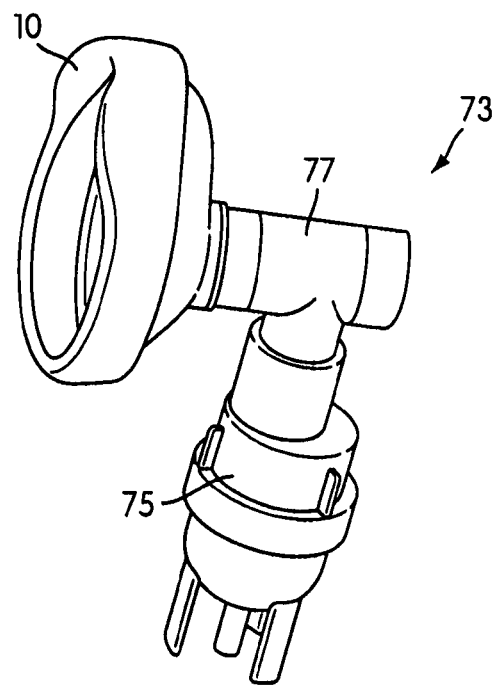
FIG. 25 is a perspective view of a mask connected to a nebulizer via an adapter in accordance with an embodiment of the present invention.

As shown in the perspective view of FIG. 25, a nebulizer and mask assembly 73 is shown and includes mask 10 and nebulizer 75. The mask 10 is shown connected to the nebulizer 75 via an adapter 77. In this embodiment, the adapter 77 has an "L" or "T" shaped configuration, so that the aerosol is directed generally orthogonal to the longitudinal axis of the nebulizer body.

Figure 26:
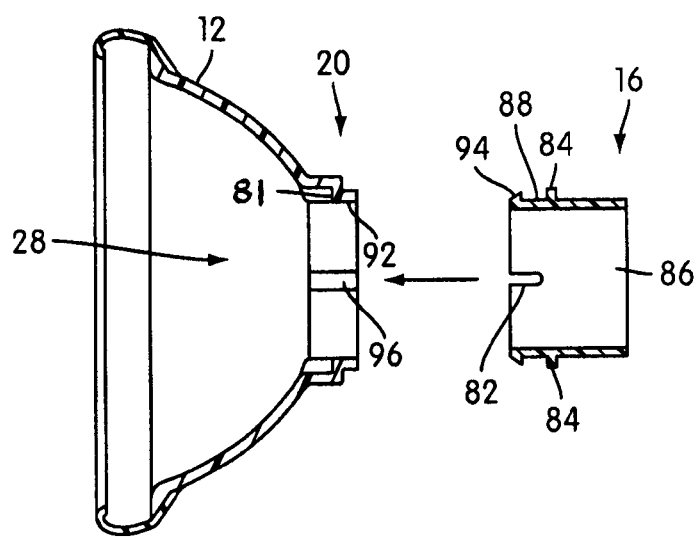
FIG. 26 is a cross-sectional view of a mask, including an adapter and an adapter attachment region in accordance with another embodiment of the present invention.
Figure 27A:
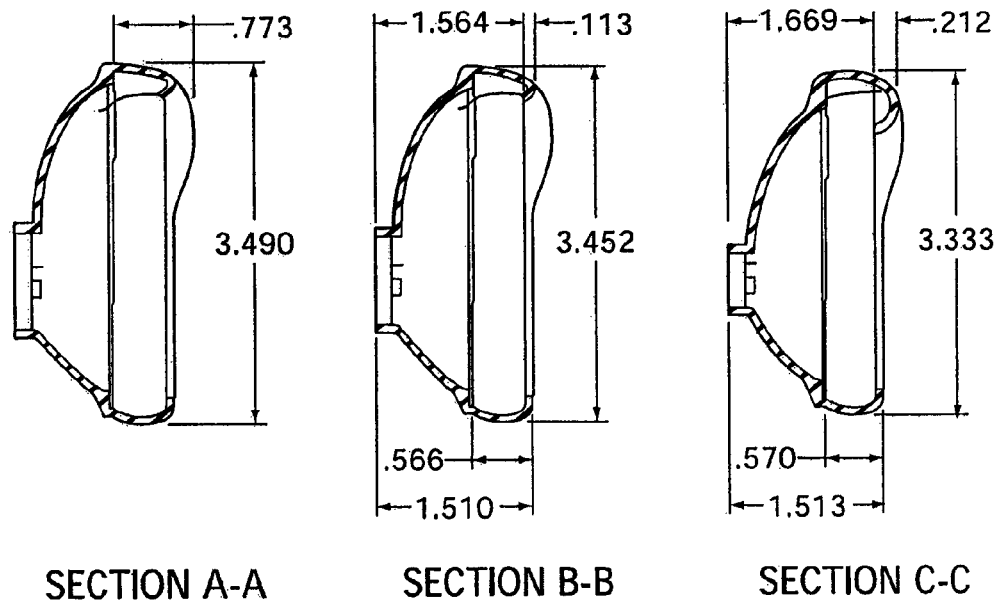
FIG. 27 is a series of longitudinal cross-sectional views taken along progressive parallel planes of a mask in accordance with an embodiment of the present invention.
Figure 27A:
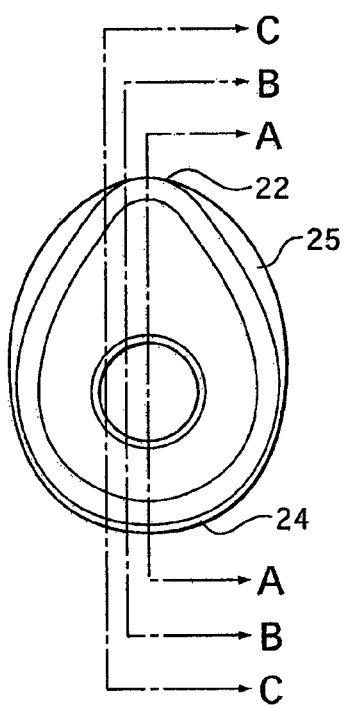
Figure 27B:
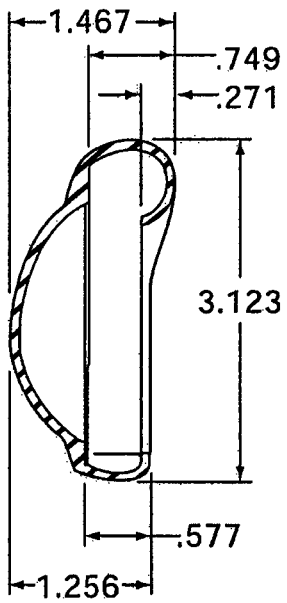
Figure 27B:
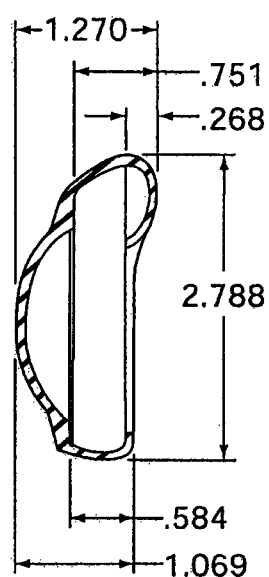
Figure 27B:
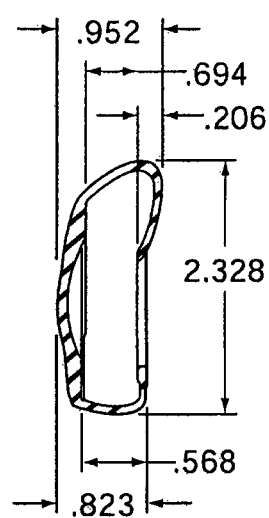
Figure 27B:
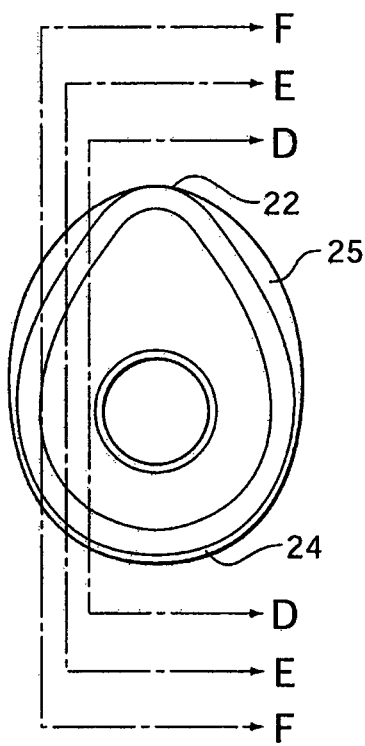
Figure 28A:
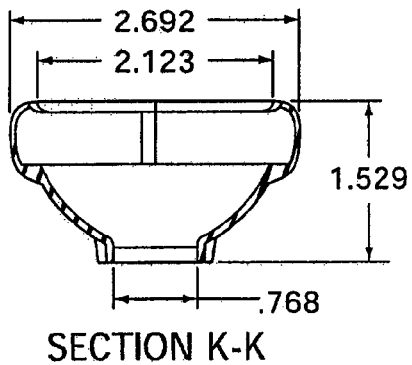
FIG. 28 is a series of lateral cross-sectional views taken along progressive parallel planes of a mask in accordance with an embodiment of the present invention.
Figure 28A:
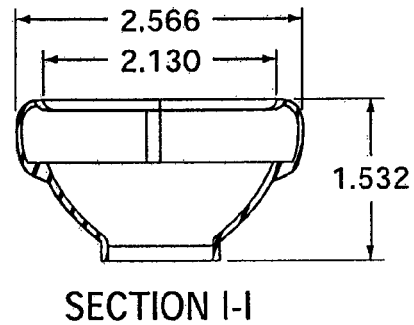
Figure 28A:
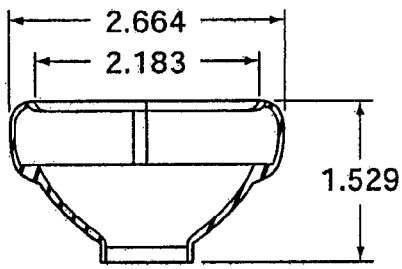
Figure 28A:
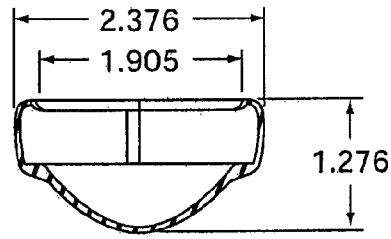
Figure 28A:
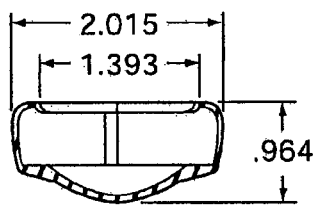
Figure 28A:
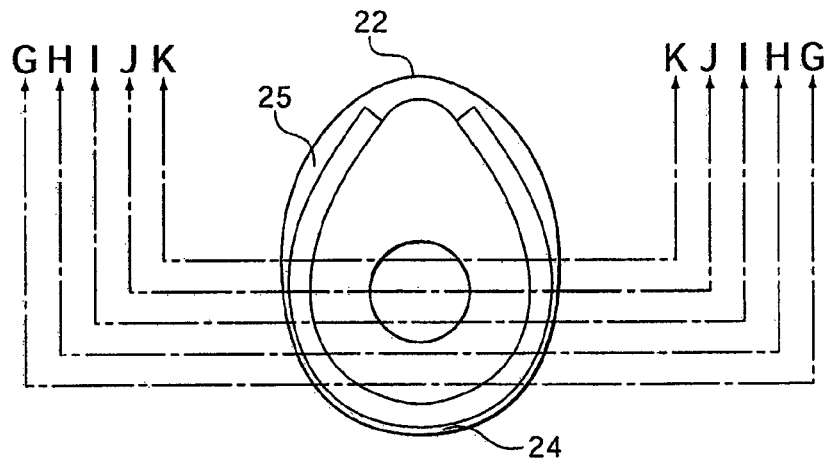
Figure 28B:
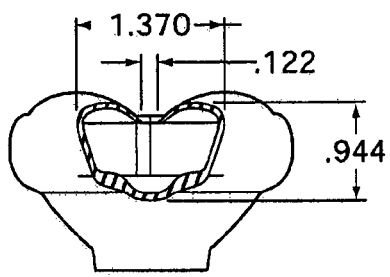
Figure 28B:
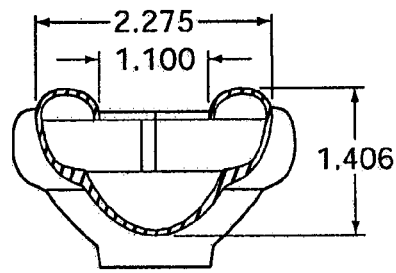
Figure 28B:
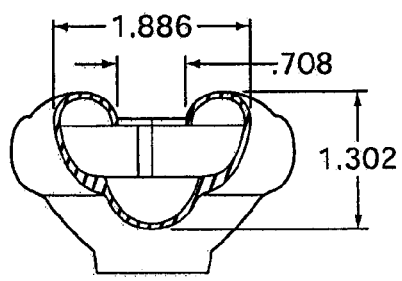
Figure 28B:
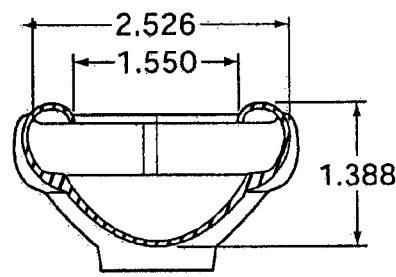
Figure 28B:
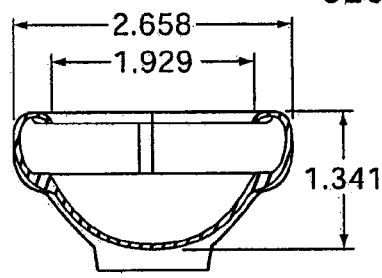
Figure 28B:
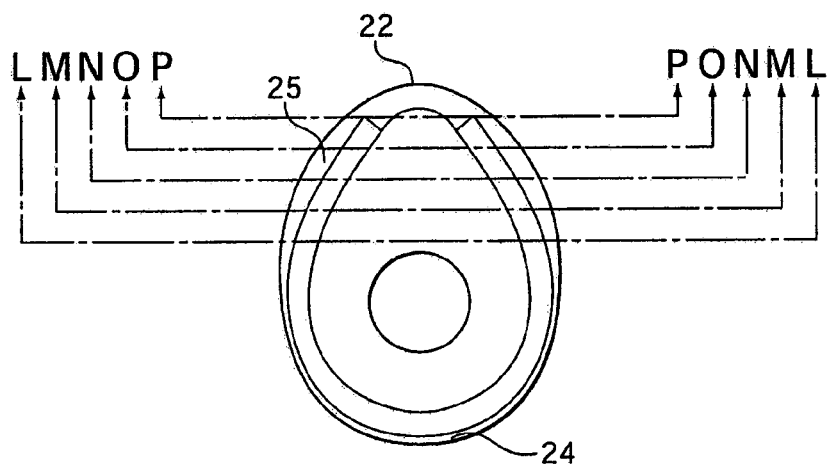

In another embodiment, shown in reference to FIG. 3 and FIG. 26, the attachment region 20 may include catches 81 that engage with tabs 88 in the adapter 16 to secure the adapter 16 in place on the mask body 12. The tabs 88 have outwardly projecting catches 94 that engage with catches 81, as shown. A rim 84 or adapter 16 prevents over-insertion of the adapter 16. As shown in FIG. 26, and with additional reference to FIG. 3, the tab 88 is defined on opposite sides thereof by a cutaway portion 90 to allow flexibility of the tab 88 during insertion of the adapter 16. That is, when the adapter 16 is being inserted into the opening 28, the outwardly projecting catches 94 of the tabs 88 are cammed to flex inward by the inner walls 92 of the opening 28. When the catches 94 reach the catches 81, they are permitted to once again expand and to lock into position, thereby retaining the adapter 16 in the mask body 12. In one embodiment, a key slot 82 may be provided in the adapter 16 that is configured to line up with a raised key 96 on the wall 92 of the opening 28 in order to properly align the adapter 16 with the mask body 12, if desired. On an opposite side, the adapter 16 may include a medication delivery mechanism attachment region 86 for connecting or otherwise communicating with a medication delivery mechanism.

It should be appreciated that the adapter 16 allows the mask to be used for several different applications. That is, various different adapters can be used to mate with the mask body 12 to enable the mask to be communicated with various aerosol output devices, such as aerosol dispensers, nebulizers, and/or spacers for metered-dose inhalers.

Figure 29:
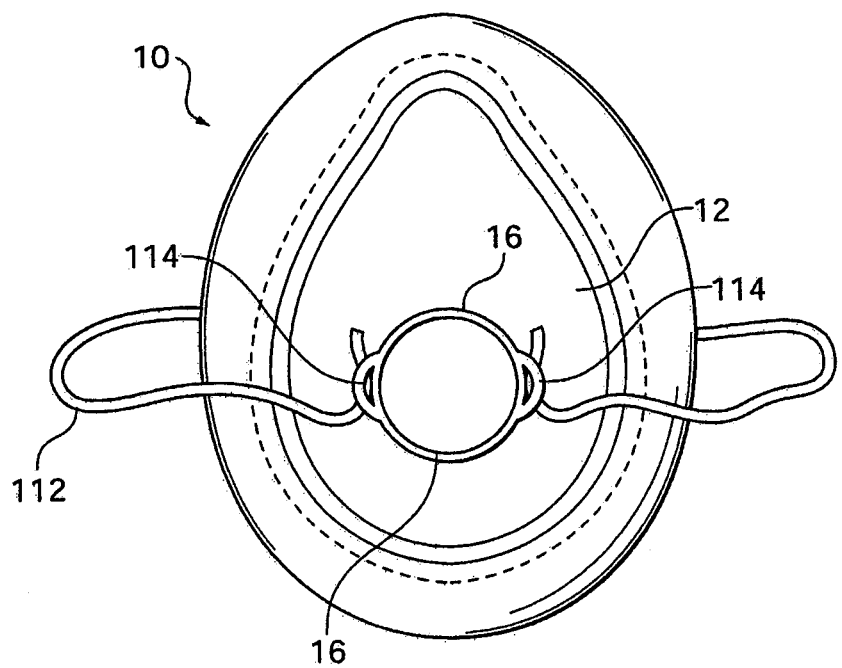
FIG. 29 is a front elevational view of a mask having a head mount attached to an adaptor in accordance with an embodiment of the present invention.
Figure 30:
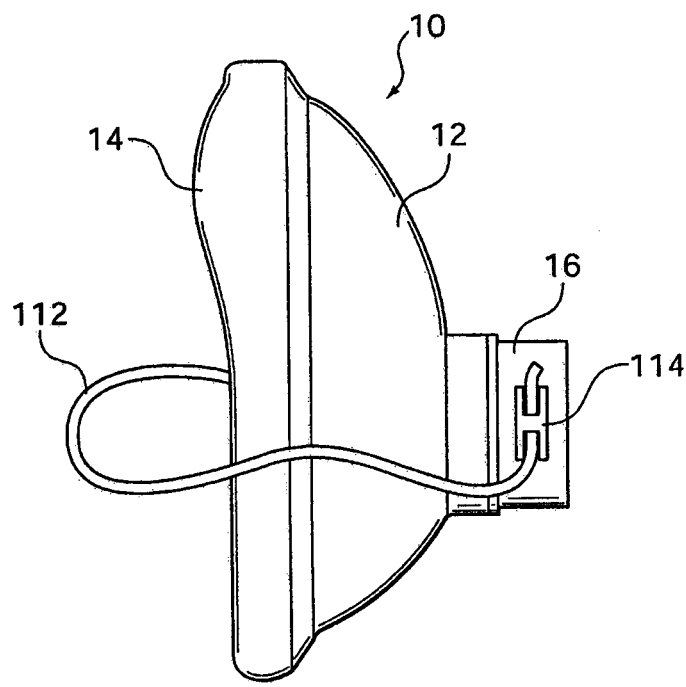
FIG. 30 is a side elevational view of a mask having a head mount attached to an adaptor in accordance with an embodiment of the present invention.
Figure 31:
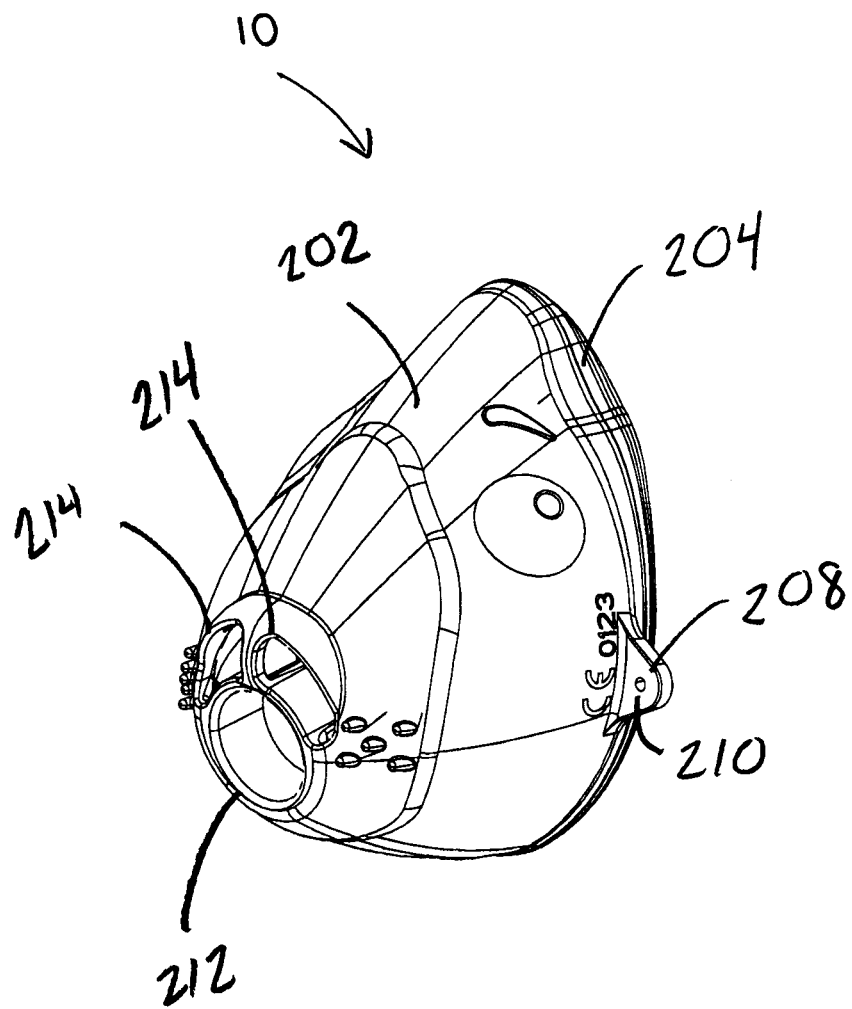
FIG. 31 is a front perspective view of a mask in accordance with an embodiment of the present invention.

In one embodiment, as illustrated in FIGS. 29 and 30, the adapter 16 is adapted to be connected with a head mount 112 that can be used to mount the mask 10 to the head of a patient. In one embodiment, the head mount 112 takes the form of straps. However, any structure that secures the mask to the head of a patient can be used. As shown in the embodiment of FIGS. 29 and 30, the head mount 112 is received within a receiving loop or loops 114 integrally formed on opposite exterior surfaces of the spacer 16 as shown. This provides an adjustable head mount, as the straps 114 can be pulled further through the loops 114 to accommodate smaller diameter head sizes. The straps 112 are retained within loops 114 by a friction fit or resilient grip applied by the resiliency of the material of the loops 114 and/or the head mount 112. It should be appreciated, however, that there are numerous ways of connecting the head mount 112 to the adaptor, such as snaps, velcro, and clips as non-limiting examples. The straps can be elastic or inelastic, and can extend around the back of the head of the patient to secure the mask on the patient, with the seal portion 14 in sealing engagement with the patient's face.

In other embodiments, for example, where the mask 10 is to be used as a spacer for a nebulizer, no head mount or strap is used or needed, as the patient simply manually holds the mask in place during use.

It should be appreciated that the removable adapter 16, with or without the headmount, can be used with a mask of a more conventional seal portion that engages the patient's face.

In one embodiment, as shown in FIGS. 31-35, the mask 10 may have a unitary construction having a body portion 202 and a seal portion 204. The mask may be formed from PVC. However, a variety of other materials could be used without departing from the scope of the present invention. The body includes a pair of ears 208 having holes 210 for receipt of the head mount 112 so that the mask can be strapped onto the patient's face 100. The body 12 further includes a central opening 212 which may be coupled to adapter 16. Spaced about central opening 212 are offset openings 214. Offset openings 214 permit the patient to exhale to the external environment as will be described in more detail below.

Figure 32:
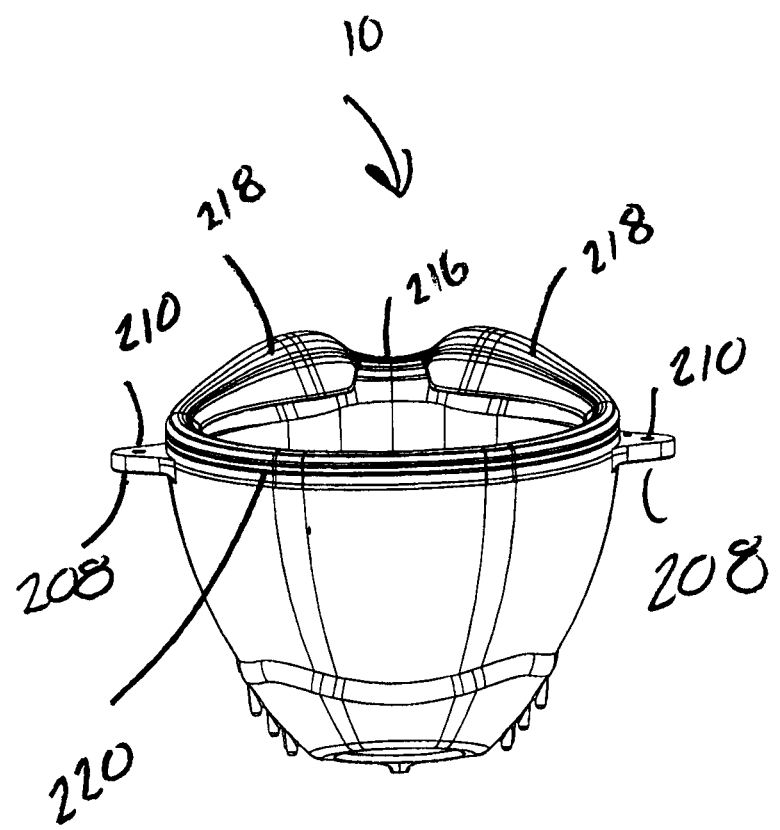
FIG. 32 is a bottom plan view of a mask in accordance with an embodiment of the present invention.
Figure 33:
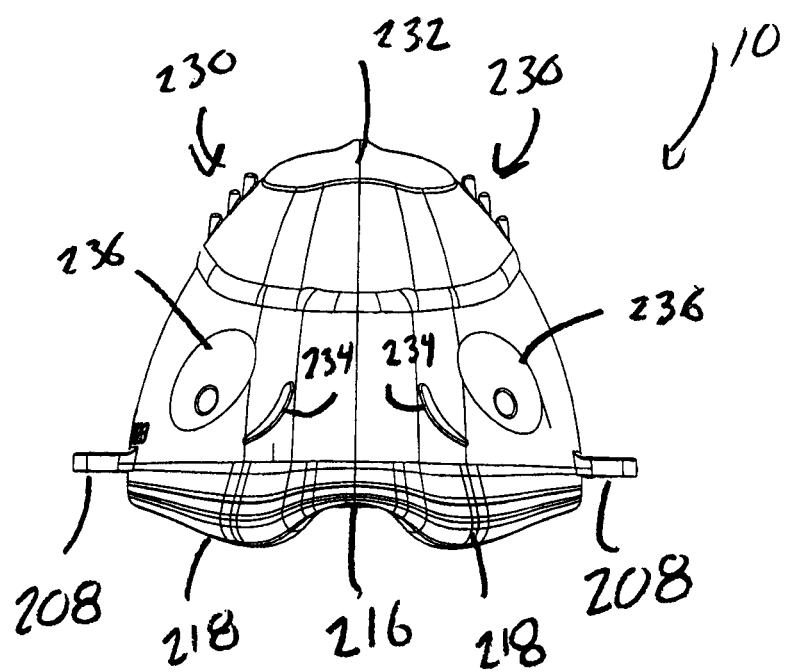
FIG. 33 is a top plan view of a mask in accordance with an embodiment of the present invention.
Figure 34:
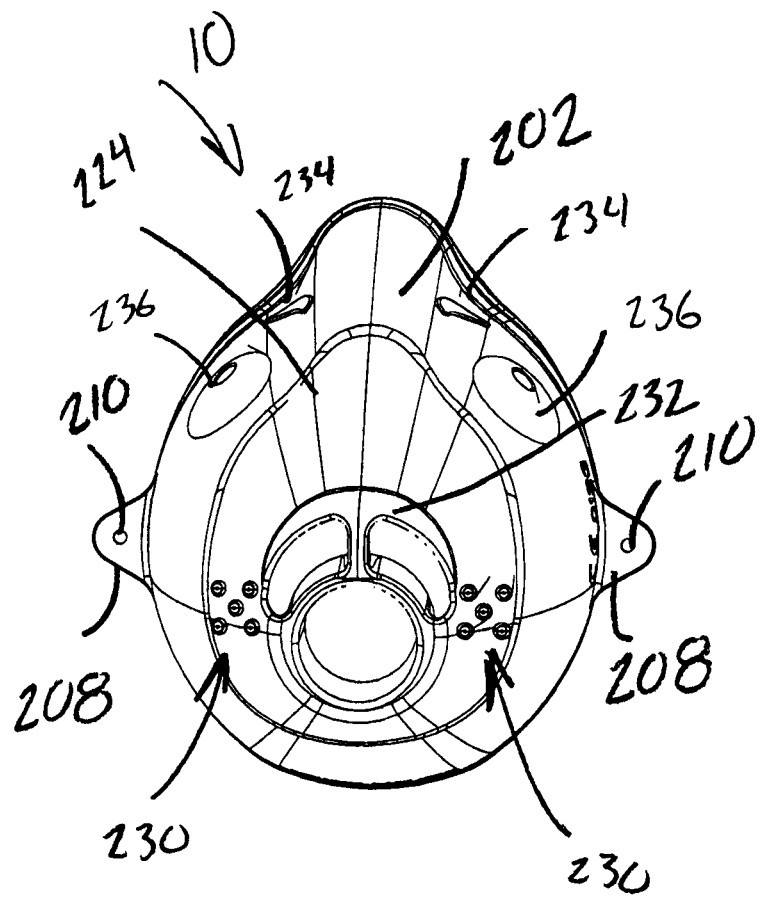
FIG. 34 is a front elevational view of a mask in accordance with an embodiment of the present invention.

As best appreciated with reference to FIGS. 32-34, the seal portion 204 includes an upper portion 216, transition portions 218, and a bottom portion 220. The transition portions 218 generally extend between the upper portion 216 and the bottom portion 220. As in the previous embodiments, the transition portions have more material in their cross-section and a greater linear length. Transition portions 218 are wider and deeper than the adjacent portions of the mask. These portions may be configured to contact the patient's face before upper portion 216 or bottom portion 220 such that the transition portions form a secure seal about the patient's eyes.

Figure 35:
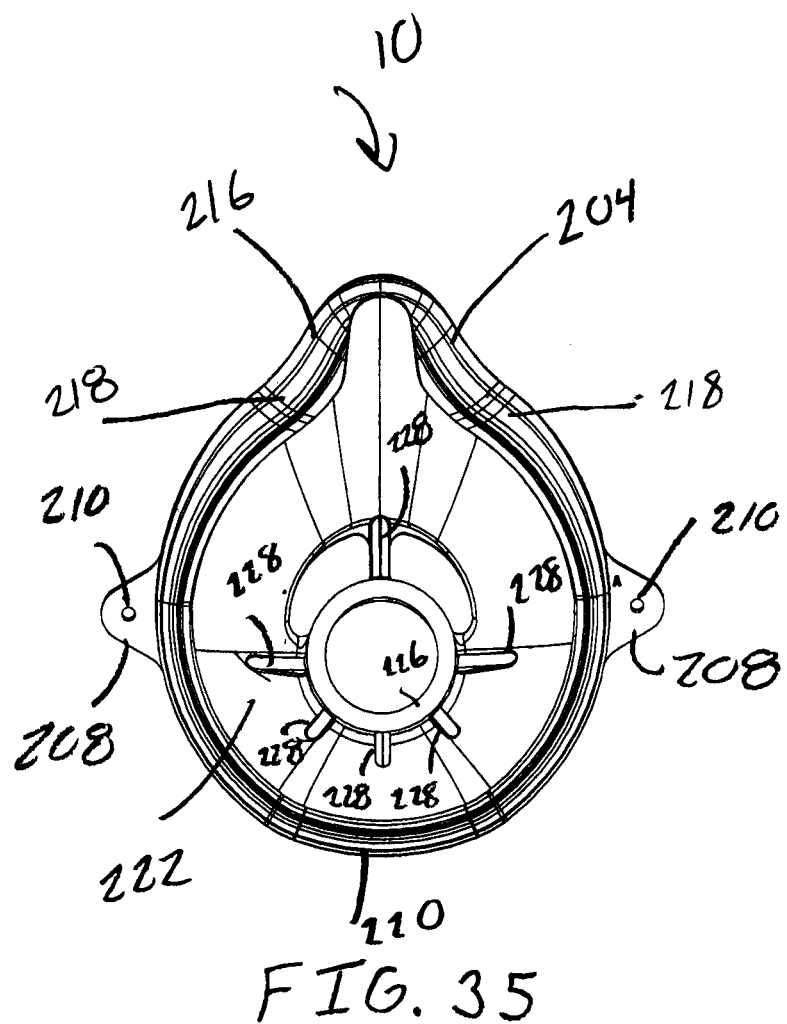
FIG. 35 is a rear elevational view of a mask in accordance with an embodiment of the present invention.

With reference to FIGS. 34 and 35, the mask has an inner surface 222 and an outer surface 224. Inner surface includes an annular ring 226 surrounded by ribs 228. Together ring 226 and ribs 228 function to provide structural support about opening 212. To provide additional structural support to the mask, the wall thickness between the inner surface and the outer surface may be altered rather than using materials with different durometers. For instance, the wall thickness of the body portion 202 may be thicker than the wall thickness of the seal portion. Outer surface 224 includes ornamental features. The ornamental features may be three-dimensional, extending from the outer surface 224, or they could be merely drawn, printed or otherwise applied to the outer surface so that the mask appeals to pediatric patients. As shown, the mask includes features so that mask 10 appears to look like a seal. These features include whiskers 230, nose 232, eyelashes 234, and eyes 236. Of course, the mask may be configured to look like a variety of different creatures.

The masks of the present invention may be used to deliver aerosolized medication to a patient. In use, transition portions 25, 218 prevent medication from escaping the mask and entering the eyes of the user. As such, it has been found that the amount of force which needs to be applied to the mask in order to create an adequate seal has been significantly reduced thereby enhancing user comfort. The embodiments shown in FIGS. 1-30 are particularly well-suited for use with pressurized Metered Dose Inhalers (pMDIs), Dry Power Inhalers (DPIs) with and without Valved Holding Chambers (VHCs), and the like. As noted above, one of the critical features of masks used in these applications is the need for an adequate seal between the mask and the face of the user. In addition, when a VHC is used, the patient must be able to generate a sufficient pressure differential in the chamber in order to open the valve. When an inadequate seal exists, many patients may find it difficult, if not impossible, to adequately open the valve. Therefore, the superior seal integrity provided by the present invention is particularly advantageous in these applications. Similarly, the embodiment shown in FIGS. 31-35 is similar in many respects to the previous embodiments; yet, it is particularly well-suited for the use with jet nebulizers and the like. Transition portions 218 once again form a seal with the face of the patient to prevent the medication-laden gas from contacting the patient's eyes. When used with jet nebulizers, it is necessary to allow excess medication laden air to freely escape the mask. To achieve this result, this embodiment includes openings 214. Openings 214 extend normally relative to the body 202 of the mask such that any exhaled medication is expelled away from the patient and the patient's eyes. Of course, the features of any of the above-described embodiments may be utilized with the features of any of the other embodiments.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mask for sealing an area around a patient's mouth and nose for delivery of an aerosol, comprising:
    a mask body having an opening for reception of the aerosol; and
    a mask seal formed around a perimeter of the mask body configured to engage a patient's face around the nose and mouth along a face-engaging surface, wherein:
        the face-engaging surface has an inner edge and an outer edge when the mask seal engages the patient's face;
        the face-engaging surface has a width as measured from a point on the inner edge to the nearest point on the outer edge;
        an inner concave surface of the mask seal forms a seal well having a depth and a width;
        the mask seal has a configuration that includes
            a generally larger radiused lower portion for engagement of the patient's face between the chin and lips and upwardly along opposite sides of the patient's mouth,
            a generally smaller radiused upper portion for engagement of the patient's face across the bridge of the patient's nose, wherein the upper portion of the mask seal has a greater length of material when measured in a direction extending away from the mask body in comparison with that at the lower portion of the mask seal, and
            a transition portion between the lower portion and the upper portion for engagement of a portion of the patient's face beneath the eyes,
        the width of the face-engaging surface along the transition portion of the mask seal adapted to touch the face beneath the eyes of the patient is larger than the width of the face-engaging surface along the upper portion or the lower portion, and
        the depth and width of the seal well along the transition portion of the mask seal are larger than the depth and width of the seal well along the upper portion or the lower portion such that:
            the transition portion of the mask seal formed around the perimeter of the mask body comprises more material than the upper portion and the lower portion; and
            the aerosol is prevented from blowing into the eyes of the patient by the transition portion.

2. The mask according to claim 1, wherein the mask body and the mask seal are integrally formed together.

3. The mask according to claim 1, wherein the mask body and the mask seal are mechanically attached together.

4. The mask according to claim 1, wherein the mask body and the mask seal are adhesively bonded together.

5. The mask according to claim 1, wherein the transition portion of the mask seal has a greater length of material when measured in a direction extending orthogonally away from the mask body in comparison with that at the upper portion and the lower portion of the mask seal such that a greater sealing force between the patient's face and the face-engaging surface is developed in the transition portion relative to the upper portion and the lower portion.

6. The mask according to claim 1, wherein the mask seal has an arcuate cross-section forming the well, and wherein the well is deeper at the transition portion in comparison with the lower portion such that the lower portion has a distal face engaging surface that extends generally along a plane, and the transition portion has a distal face engaging surface that bulges outwardly from the plane, the bulging being entirely above the mouth of the patient in proximity to the portion of the patient's face beneath the eyes.

7. The mask according to claim 1, wherein the mask seal has an arcuate cross-section forming the well, and wherein the well is wider at the transition portion in comparison with the lower portion.

8. The mask of claim 1, wherein the seal well of the mask seal is opened towards a direction facing away from the face-engaging surface of the mask seal.

9. A mask for sealing an area around a patient's mouth and nose for delivery of an aerosol, comprising:
   a mask body having an opening for reception of the aerosol; and
   a mask seal formed around a perimeter of the body and being configured to engage a patient's face around the nose and mouth, wherein the mask seal has a configuration that includes,
      a generally larger radiused lower portion for engagement of the patient's face between the chin and lips and upwardly along opposite sides of the patient's mouth,
      a generally smaller radiused upper portion for engagement of the patient's face across the bridge of the patient's nose, wherein the lower portion has a distal face engaging surface that extends generally along a plane, and the transition portion has a distal face engaging surface that bulges outwardly from the plane, the bulging being configured to be entirely above the mouth of the patient in proximity to the portion of the patient's face beneath the eyes, and
      a transition portion between the lower portion and the upper portion for engagement of a portion of the patient's face beneath the eyes, and wherein the transition portion of the mask seal adapted to touch the face beneath the eyes of the patient has a greater surface area of contact with the patient's face than the lower portion of the mask seal when the mask seal is disposed in sealing engagement with the patient's face such that:
         the transition portion of the mask seal formed around the perimeter of the mask body comprises more material than the upper portion and the lower portion; and
         the aerosol is prevented from blowing into the eyes of the patient by the transition portion.

10. The mask according to claim 9, further comprising an adapter configured for attachment to the opening and constructed and arranged to enable the mask body to be connected to a medication delivery mechanism.

11. The mask according to claim 9, wherein the mask seal is partially tubular-shaped.

12. The mask according to claim 9, wherein the mask body and the mask seal are integrally formed together.

13. The mask according to claim 9, wherein the mask body and the mask seal are mechanically attached together.

14. The mask according to claim 9, wherein the mask body and the mask seal are adhesively bonded together.

15. A mask for sealing an area around a patient's mouth and nose for delivery of an aerosol, comprising:
   a mask body having an opening for reception of the aerosol; and
   a mask seal connected to the body around a perimeter of the body and being configured to engage a patient's face around the nose and mouth, wherein:
      the mask seal has a configuration that includes a generally larger radiused lower portion for engagement of the patient's face between the chin and lips and upwardly along opposite sides of the patient's mouth, a generally smaller radiused upper portion for engagement of the patient's face across the bridge of the patient's nose, and a transition portion between the lower portion and the upper portion for engagement of a portion of the patient's face beneath the eyes;
      the transition portion is adapted to engage the patient's face along opposite sides of the patient's nose; and
      the lower portion has a distal face engaging surface that extends generally along a plane, and the transition portion has a distal face engaging surface that bulges outwardly from the plane, the bulging adapted to be entirely above the mouth of the patient in proximity to the portion of the patient's face beneath the eyes such that:
         the transition portion of the mask seal formed around the perimeter of the mask body comprises more material than the upper portion and the lower portion; and
         the aerosol is prevented from blowing into the eyes of the patient by the transition portion.

16. The mask according to claim 15, wherein the upper portion of the mask seal has a greater length of material when measured in a direction extending orthogonally away from the mask body in comparison with that at the lower portion of the mask seal.

17. The mask according to claim 15, wherein the transition portion of the mask seal has a greater length of material when measured in a direction extending orthogonally away from the mask body in comparison with that at the upper portion and the lower portion of the mask seal such that a greater sealing force between the patient's face and the mask seal is developed in the transition portion relative to the upper portion and the lower portion.

18. The mask according to claim 15, wherein the mask body is formed from polycarbonate and the mask seal is formed from silicone.

19. The mask according to claim 15, wherein the mask seal has an arcuate cross-section forming a well, and wherein the well is deeper at the transition portion in comparison with the lower portion.

20. The mask according to claim 15, wherein the mask seal has an arcuate cross-section forming a well, and wherein the well is wider at the transition portion in comparison with the lower portion.

21. The mask according to claim 15, further comprising an adapter configured for attachment to the opening and constructed and arranged to enable the mask body to be connected to a medication delivery mechanism.

22. The mask according to claim 15, wherein the mask seal is partially tubular-shaped.

23. The mask according to claim 15, wherein the mask body and the mask seal are integrally formed together.

24. The mask according to claim 15, wherein the mask body and the mask seal are mechanically attached together.

25. The mask according to claim 15, wherein the mask body and the mask seal are adhesively bonded together.

* * * * *